(12) United States Patent
Manalili Wheeler et al.

(10) Patent No.: US 9,752,173 B2
(45) Date of Patent: Sep. 5, 2017

(54) COMPOSITIONS AND METHODS FOR INHIBITING TERMINAL TRANSFERASE ACTIVITY

(71) Applicants: IBIS BIOSCIENCES, INC., Carlsbad, CA (US); Nina M. Hofstadler, Vista, CA (US)

(72) Inventors: Sherilynn Manalili Wheeler, Carlsbad, CA (US); James C. Hannis, Carlsbad, CA (US); Steven A. Hofstadler, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 150 days.

(21) Appl. No.: 14/754,262

(22) Filed: Jun. 29, 2015

(65) Prior Publication Data
US 2015/0376671 A1 Dec. 31, 2015

Related U.S. Application Data

(63) Continuation of application No. 13/081,272, filed on Apr. 6, 2011, now Pat. No. 9,068,017.

(60) Provisional application No. 61/322,195, filed on Apr. 8, 2010.

(51) Int. Cl.
| | |
|---|---|
| C12P 19/34 | (2006.01) |
| C07K 14/47 | (2006.01) |
| C07K 14/54 | (2006.01) |
| C12Q 1/68 | (2006.01) |
| C07H 21/02 | (2006.01) |

(52) U.S. Cl.
CPC .......... *C12P 19/34* (2013.01); *C07K 14/4703* (2013.01); *C07K 14/5406* (2013.01); *C12Q 1/686* (2013.01)

(58) Field of Classification Search
CPC .............. C12Q 1/686; C12Q 2521/131; C12Q 2525/161; C12Q 2527/125; C12Q 2565/627
See application file for complete search history.

(56) References Cited

U.S. PATENT DOCUMENTS

| | | | |
|---|---|---|---|
| 4,458,066 A | 7/1984 | Caruthers et al. |
| 5,338,671 A | 8/1994 | Scalice et al. |
| 5,494,810 A | 2/1996 | Barany et al. |
| 5,508,169 A | 4/1996 | Deugau et al. |
| 5,639,611 A | 6/1997 | Wallace et al. |
| 5,773,258 A | 6/1998 | Birch et al. |
| 5,965,408 A | 10/1999 | Short |
| 6,090,590 A | 7/2000 | Kao |
| 7,108,974 B2 | 9/2006 | Ecker et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,312,036 B2 | 12/2007 | Sampath et al. |
| 7,339,051 B2 | 3/2008 | Crooke et al. |
| 7,662,594 B2 | 2/2010 | Kong et al. |
| 2003/0027135 A1 | 2/2003 | Ecker et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0225529 A1 | 12/2003 | Ecker et al. |
| 2003/0228571 A1 | 12/2003 | Ecker et al. |
| 2004/0110169 A1 | 6/2004 | Ecker et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0161770 A1 | 8/2004 | Ecker et al. |
| 2004/0185438 A1 | 9/2004 | Ecker |
| 2004/0202997 A1 | 10/2004 | Ecker et al. |

(Continued)

FOREIGN PATENT DOCUMENTS

| | | |
|---|---|---|
| WO | WO-02070664 A2 | 9/2002 |
| WO | WO-03001976 A2 | 1/2003 |

(Continued)

OTHER PUBLICATIONS

Advisory Action mailed Feb. 19, 2014 for U.S. Appl. No. 13/081,272, filed Apr. 6, 2011.
Applicant Initiated Interview Summary mailed Jan. 28, 2015 for U.S. Appl. No. 13/081,272, filed Apr. 6, 2011.
Ballabio A., et al., "Screening for Steroid Sulfatase (STS) Gene Deletions by Multiplex DNA Amplification," Human Genetics, 1990, vol. 84 (6), pp. 571-573.
Beaucage S.L., et al., "Deoxynucleoside Phosphoramidites—A New Class of Key Intermediates for Deoxypolynucleotide Synthesis," Tetrahedron Letters, 1981, vol. 22 (20), pp. 1859-1862.
Blyn B., et al., "Rapid Detection and Molecular Serotyping of Adenovirus by Use of PCR Followed by Electrospray Ionization Mass Spectrometry," Journal of Clinical Microbiology, 2008, vol. 46 (2), pp. 644-651.

(Continued)

*Primary Examiner* — Teresa Strzelecka
(74) *Attorney, Agent, or Firm* — David A. Casimir; Casimir Jones, S.C.

(57) ABSTRACT

The present invention realtes to systems and methods for amplifying nucleic acid. In particular, systems and methods are provided for inhibiting polymerase based terminal transferase activity within a polynucleotide amplification setting (e.g., polymerase chain reaction). In addition, systems and methods are provided for generating amplified products generated with polynucleotide amplification techniques having reduced 3' non-templated nucleotide addition.

3 Claims, 1 Drawing Sheet

(56) References Cited

U.S. PATENT DOCUMENTS

| | | |
|---|---|---|
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0027459 A1 | 2/2005 | Ecker et al. |
| 2005/0123952 A1 | 6/2005 | Griffey et al. |
| 2005/0130196 A1 | 6/2005 | Hofstadler et al. |
| 2005/0142581 A1 | 6/2005 | Griffey et al. |
| 2005/0164215 A1 | 7/2005 | Hofstadler et al. |
| 2005/0266397 A1 | 12/2005 | Ecker et al. |
| 2005/0270191 A1 | 12/2005 | Hofstadler et al. |
| 2006/0014154 A1 | 1/2006 | Eshoo |
| 2006/0057619 A1 | 3/2006 | London et al. |
| 2006/0121520 A1 | 6/2006 | Ecker et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2006/0275749 A1 | 12/2006 | Sampath et al. |
| 2006/0275788 A1 | 12/2006 | Ecker et al. |
| 2007/0087336 A1 | 4/2007 | Sampath et al. |
| 2007/0087337 A1 | 4/2007 | Sampath et al. |
| 2007/0087338 A1 | 4/2007 | Sampath et al. |
| 2007/0087339 A1 | 4/2007 | Sampath et al. |
| 2007/0087340 A1 | 4/2007 | Sampath et al. |
| 2007/0087341 A1 | 4/2007 | Sampath et al. |
| 2007/0184434 A1 | 8/2007 | Sampath et al. |
| 2007/0202525 A1 | 8/2007 | Quake et al. |
| 2007/0218467 A1 | 9/2007 | Ecker et al. |
| 2007/0218489 A1 | 9/2007 | Sampath et al. |
| 2007/0224614 A1 | 9/2007 | Sampath et al. |
| 2007/0238116 A1 | 10/2007 | Sampath et al. |
| 2007/0243544 A1 | 10/2007 | Sampath et al. |
| 2007/0248969 A1 | 10/2007 | Sampath et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0047665 A1 | 2/2009 | Hall et al. |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |

FOREIGN PATENT DOCUMENTS

| | | |
|---|---|---|
| WO | WO-03100035 A2 | 12/2003 |
| WO | WO-2004009849 A1 | 1/2004 |
| WO | WO-2004052175 A2 | 6/2004 |
| WO | WO-2004053076 A2 | 6/2004 |
| WO | WO-2004053141 A2 | 6/2004 |
| WO | WO-2004053164 A1 | 6/2004 |
| WO | WO-2004060278 A2 | 7/2004 |
| WO | WO-2004093644 A2 | 11/2004 |
| WO | WO-2004101809 A2 | 11/2004 |
| WO | WO-2004111187 A2 | 12/2004 |
| WO | WO-2005023083 A2 | 3/2005 |
| WO | WO-2005023091 A2 | 3/2005 |
| WO | WO-2005023986 A2 | 3/2005 |
| WO | WO-2005024046 A2 | 3/2005 |
| WO | WO-2005033271 A2 | 4/2005 |
| WO | WO-2005036369 A2 | 4/2005 |
| WO | WO-2005086634 A2 | 9/2005 |
| WO | WO-2005089128 A2 | 9/2005 |
| WO | WO-2005091971 A2 | 10/2005 |
| WO | WO-2005092059 A2 | 10/2005 |
| WO | WO-2005094421 A2 | 10/2005 |
| WO | WO-2005098047 A2 | 10/2005 |
| WO | WO-2005116263 A2 | 12/2005 |
| WO | WO-2005117270 A2 | 12/2005 |
| WO | WO-2006019784 A2 | 2/2006 |
| WO | WO-2006034294 A1 | 3/2006 |
| WO | WO-2006071241 A2 | 7/2006 |
| WO | WO-2006094238 A2 | 9/2006 |
| WO | WO-2006116127 A2 | 11/2006 |
| WO | WO-2006135400 A2 | 12/2006 |
| WO | WO-2007014045 A2 | 2/2007 |
| WO | WO-2007047778 A2 | 4/2007 |
| WO | WO-2007086904 A2 | 8/2007 |
| WO | WO-2007100397 A2 | 9/2007 |
| WO | WO-2007118222 A2 | 10/2007 |

OTHER PUBLICATIONS

Borate Buffer, Cold Sprig Harbor Protocols Online (2009); Retrieved from URL: <http://cshprotocols.cshlp.org/content/2009/7/pdb.rec11857.full?text_only=true>.

Brown E.L., et al., "Chemical Synthesis and Cloning of a Tyrosine tRNA Gene," Methods in Enzymology, 1979, vol. 68, pp. 109-151.

Bustin S.A., et al., "Absolute Quantification of mRNA Using Real-time Reverse Transcription Polymerase Chain Reaction Assays," Journal of Molecular Endocrinology, 2000, vol. 25 (2), pp. 169-193.

Chamberlain J. S., et al., "Deletion screening of the Duchenne muscular dystrophy locus via multiplex DNA amplification", Nucleic Acids Res., 1988, 16 (23), 11141-11156.

Don R.H., et al., "Touchdown PCR to Circumvent Spurious Priming during Gene Amplification," Nucleic Acids Research, 1991, vol. 19 (14), pp. 4008.

Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.

Ecker D.J., et al., "The Microbial Rosetta stone Database: A Compilation of Global and Emerging Infectious Microorganisms and Bioterrorist Threat Agents," BMC Microbiology, 2005, vol. 5, pp. 19.

Ecker J.A., et al., "Identification of Acinetobacter Species and Genotyping of Acinetobacter Baumannii by Multilocus PCR and Mass Spectrometry," Journal of Clinical Microbiology, 2006, vol. 44 (8), pp. 2921-2932.

Final Office Action mailed Dec. 19, 2013 for U.S. Appl. No. 13/081,272, filed Apr. 6, 2011.

Gill P., et al., "Nucleic Acid Isothermal Amplification Technologies: A Review," Nucleosides, Nucleotides and Nucleic Acids, vol. 27 (3), pp. 224-243.

Guilfoyle R.A., et al., "Ligation-Mediated PCR Amplification of Specific Fragments from a Class-li Restriction Endonuclease Total Digest," Nucleic Acids Research, 1997, vol. 25 (9), pp. 1854-1858.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hannis J.C., et al., "High-Resolution Genotyping of Campylobacter Species by Use of PCR and High-Throughput Mass Spectrometry," Journal of Clinical Microbiology, 2008, vol. 46 (4), pp. 1220-1225.

Hayden M.J., et al., "Multiplex-Ready PCR: A New Method for Multiplexed SSR and SNP Genotyping," BMC Genomics, 2008, vol. 9, pp. 80.

Hecker K.H., et al., "High and Low Annealing Temperatures Increase both Specificity and Yield in Touchdown and Step-down PCR," Biotechniques, 1996, vol. 20 (3), pp. 478-485.

Herman J.G., et al., "Methylation-Specific PCR: A Novel PCR Assay for Methylation Status of Cpg Islands," Proceedings of the National Academy of Sciences, 1996, vol. 93 (18), pp. 9821-9826.

Higuchi R., et al., "A General Method of in Vitro Preparation and Specific Mutagenesis of DNA Fragments: Study of Protein and DNA Interactions," Nucleic Acids Research, 1988, vol. 16 (15), pp. 7351-7367.

Higuchi R., et al., "Simultaneous Amplification and Detection of Specific DNA Sequences," Biotechnology, 1992, vol. 10 (4), pp. 413-417.

Higuchi R., et al., "Kinetic PCR Analysis: Real-Time Monitoring of DNA Amplification Reactions," Biotechnology, 1993, vol. 11 (9), pp. 1026-1030.

(56) References Cited

OTHER PUBLICATIONS

Hofstadler S.A., et al., "Selective Ion Filtering by Digital Thresholding: A Method to Unwind Complex ESI-Mass Spectra and Eliminate Signals from Low Molecular Weight Chemical Noise," Analytical Chemistry, 2006, vol. 78 (2), pp. 372-378.

Hofstadler S.A., et al., "TIGER: The Universal Biosensor," International Journal of Mass Spectrometry, 2005, vol. 242, pp. 23-41.

Hu G., et al., "DNA Polymerase-Catalyzed Addition of Nontemplated Extra Nucleotides to the 3' End of a DNA Fragment," DNA and Cell Biology, 1993, vol. 12 (8), pp. 763-770.

Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.

Kalinina O., et al., "Nanoliter Scale PCR with TaqMan Detection," Nucleic Acids Research, 1997, vol. 25 (10), pp. 1999-2004.

Krupp G., "RNA Synthesis: Strategies for the Use of Bacteriophage RNA Polymerases," Gene, 1988, vol. 72 (1-2), pp. 75-89.

Matteucci M.D., et al., "Synthesis of Deoxyoligonucleotides on a Polymer Support," Journal of the American Chemical Society, 1981, vol. 103 (11), pp. 3185-3191.

Milligan J.F., et al., "Oligoribonucleotide Synthesis Using T7 RNA polymerase and Synthetic DNA Templates," Nucleic Acids Research, 1987, vol. 15 (21), pp. 8783-8798.

Narang S.A., et al., "Improved Phosphotriester Method for the Synthesis of Gene Fragments," Methods in Enzymology, 1979, vol. 68, pp. 90-98.

Non-Final Office Action mailed Jun. 11, 2013 for U.S. Appl. No. 13/081,272, filed Apr. 6, 2011.

Non-Final Office Action mailed Aug. 12, 2014 for U.S. Appl. No. 13/081,272, filed Apr. 6, 2011.

Notice of Allowance mailed Mar. 3, 2015 for U.S. Appl. No. 13/081,272, filed Apr. 6, 2011.

Roux K.H., "Optimization and Troubleshooting in PCR," PCR Methods and Applications, 1995, vol. 4 (5), pp. S185-S194.

Roux K.H., "Using Mismatched Primer-Template Pairs in Touchdown PCR," Biotechniques, 1994, vol. 16 (5), pp. 812-814.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Schouten J.P., et al., "Relative Quantification of 40 Nucleic Acid Sequences by Multiplex Ligation-dependent Probe Amplification," Nucleic Acids Research, 2002, vol. 30 (12), pp. e57.

Triglia T., et al., "A Procedure for In Vitro Amplification of DNA Segments That Lie Outside the Boundaries of Known Sequences," Nucleic Acids Research, 1988, vol. 16 (16), pp. 8186.

Vogelstein B., et al., "Digital PCR," Proceedings of the National Academy of Sciences, 1999, vol. 96 (16), pp. 9236-9241.

Well 13
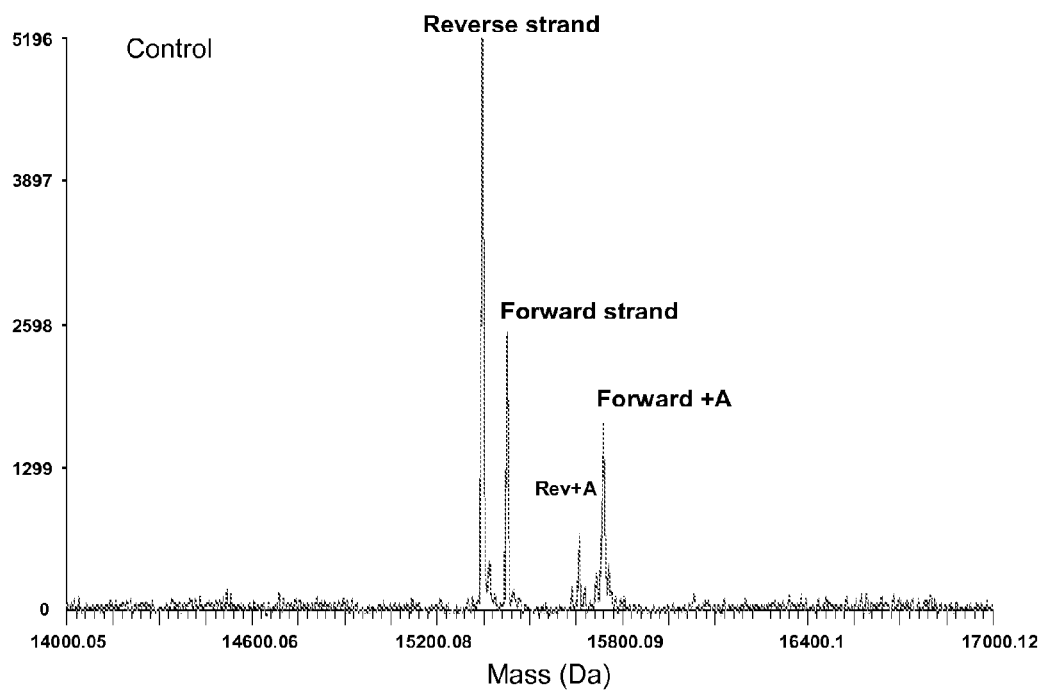
Well 75
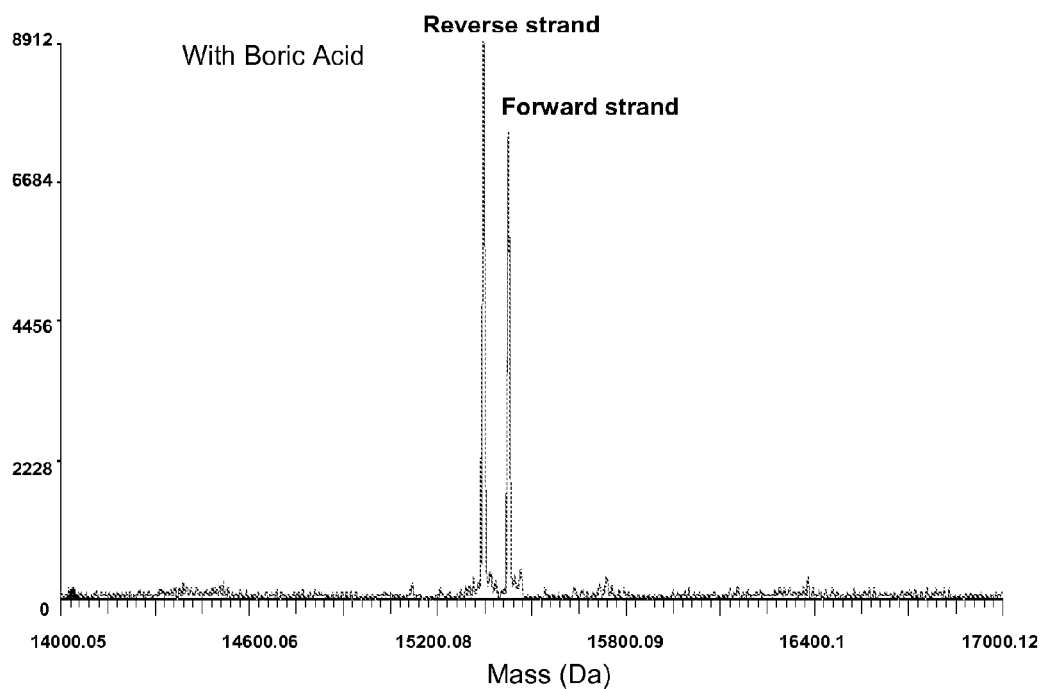

COMPOSITIONS AND METHODS FOR INHIBITING TERMINAL TRANSFERASE ACTIVITY

CROSS-REFERENCE TO RELATED APPLICATIONS

The present application claims priority to U.S. Provisional Application Ser. No. 61/322,195, filed Apr. 8, 2010, the entirety of which is herein incorporated by reference.

FIELD OF THE INVENTION

The present invention relates to systems and methods for amplifying nucleic acid. In particular, systems and methods are provided for inhibiting the terminal transferase activity of polymerases. In addition, systems and methods are provided for generating amplified products having reduced 3' non-templated nucleotide addition when generated from amplification reactions.

BACKGROUND OF THE INVENTION

Polynucleotide amplification techniques such as the polymerase chain reaction (PCR) are widely used to amplify polynucleotides for a wide variety of applications, including structural and biochemical studies and diagnotics techniques. Despite its usefulness, a number of undesired reactions increase the complexity of the polymerase products and necessitate careful purification or other approaches to reduce the impact of the undesired reactions. These reactions include the synthesis of oligonucleotides aborted during the initiation of transcription, the use of alternative template initiation sites, polymerase slippage, and the addition of one or more non-templated nucleotides at the 3' termini of nascent transcripts (e.g., through polymerase based terminal transferase activity).

What are needed are new approaches to reduce or eliminate undersired reactions or the impact of undersired reactions.

SUMMARY

Generally, polynucleotide amplification techniques such as the polymerase chain reaction (PCR) relate to a process for amplifying nucleic acids and involve the use of oligonucleotide primers, an agent for polymerization, a target nucleic acid template and successive cycles of denaturation of nucleic acid and annealing and extension of the primers to produce a large number of copies of a particular nucleic acid segment.

PCR was first developed in the 1980s as a method of copying template DNA. In its classic form, the reaction may include DNA polymerase, building block deoxynucleotide triphosphates (dATP, dTTP, dGTP and dCTP), sequence-specific forward and reverse primer oligonucleotides, a reaction buffer, the template DNA and a thermal cycler. Classically, the PCR reaction begins with a first step (denaturing/melting) at a higher temperature which melts apart the template-paired strands of DNA. This is followed by a second step at a lower temperature (primer annealing) in which the forward and reverse primers attach to the conjugate sequences on the template DNA. The third step (extension/elongation) is at an intermediate temperature in which the DNA polymerase extends the primers by adding paired deoxynucleotides and thus creating the copied deoxynucleic acid strands (cDNA) (e.g., amplicons). These three steps are repeated sequentially with a doubling of the product oligonucleotide during each cycle. Typically, the reaction is run for 15 to 40 total cycles. Over the years, many different forms of PCR have been developed, including PCR employing one to many primers (or self-priming), single- or two-temperature PCR, reactions on solid surfaces, reactions in micro- or nanoenvironments, and the like.

Terminal transferase activity involves the enzymatic catalysis of a reaction in which nucleotide triphosphates (including extension terminating nucleotides) are covalently attached to the 3' terminus of an oligonucleotide primer or primer extension product in a template independent manner. Thus, by mixing an enzyme having terminal transferase activity (e.g., Taq polymerase) with an oligonucleotide having a free 3'-OH (or functional equivalent to) and with a nucleotide triphosphate, one or more nucleotides are added to the 3' prime terminus of the oligonucleotide, irrespective of the presence or absence of a template complementary to the oligonucleotide. Terminal transferase activity can be a major contributing factor to heterogeneity in transcription products (see, e.g., Milligan et al., 1987, Nucl. Acid Res. 15:8783-8798; Krupp, 1988, Gene 72: 75-89; each herein incorporated by reference in their entireties). Terminal transferase activity is associated with many types of polymerases including, but not limited to, Taq polymerase, T7 RNA polymerase, Klenow, HIV reverse transcriptase, and 3D$^{pol}$ RNA-dependent RNA polymerase (see, e.g., U.S. Pat. No. 6,090,590; herein incorporated by reference in its entirety).

In many applications, generating PCR products having 3' non-templated nucleotide addition is undesirable. For example, non-templated addition to the 3' end of a PCR product decreases the sensitivity while increasing the complexity of assays relying on PCR amplification due to the increased number of reaction products (e.g., forward strand, reverse strand, forward strand plus non-templated addition, reverse strand plus non-templated addition) as opposed to PCR products having only blunt ends (e.g., lacking non-templated addition).

Overcoming undesired terminal transferase activity within a PCR setting has been a complex problem. Existing solutions all have disadvantages. For example, the use of low concentration magnesium salts in reaction buffers reduces terminal transferase activity. This solution, however, is undesirable in settings wherein high concentration magnesium salts are desired or needed. The use of a polymerase void of terminal transferase activity prevents 3' non-templated nucletoide addition. This solution, however, requires the use of expensive polymerases, discouraging routine use or use in high-throughput settings.

The present invention provides compositions and methods for inhibiting terminal transferase activity in amplification reactions employing polymerases that have terminal transferase activity (e.g., PCR, ligase chain reaction (LCR), etc.). For example, in some embodiments, boric acid is provided in reaction mixtures containing a polymerase to reduce 3' non-template nucleotide addition. Accordingly, in some embodiments, the present invention provides methods for generating amplification products with reduced 3' non-templated nucleotide addition. In some embodiments, the methods involve providing boric acid and an amplification reaction solution (e.g., buffer, reaction mixture, etc.) having, inter alia, a polymerase having terminal transferase activity, combining the boric acid with the reaction solution, and performing nucleic acid amplification with the combined boric acid and the reaction solution such that amplification products are generated with reduced 3' non-templated nucleotide addition relative to a reaction lacking the boric acid.

The methods are not limited to a particular polymerase having terminal transferase activity. Examples of polymerases having terminal transferase activity include, but are not limited to, Taq polymerase, T7 RNA polymerase, Klenow, HIV reverse transcriptase, and 3D$^{pol}$ RNA-dependent RNA polymerase.

The methods are not limited to a particular formulation of boric acid. In some embodiments, the boric acid is provided in an amount such that the mixture in which amplification occurs has a boric acid concentration of from 50 to 500 mM. In some embodiments, the concentration is from 100 to 200 mM. In some embodiments, the concentration is at least 50 mM (e.g., at least 100 mM). Any concentration that provides the intended benefit may be used.

The methods are not limited to any particular amplication approach. The methods may be employed in any amplication reaction in which a polymerase having terminal transferase activity is present. For example, any of a wide variety of PCR techniques benefit from the compositions and methods of the invention. Examples of PCR techniques include, but are not limited to, allele-specific PCR, assembly PCR, asymmetric PCR, digital PCR, helicase-dependent amplification, Hot-start PCR, intersequence-specific PCR, inverse PCR, ligation-mediated PCR, methylation-specific PCR, miniprimer PCR, multiplex ligation-dependent probe amplification, nested PCR, overlap-extension PCR, real-time PCR, reverse transcription PCR, solid phase PCR, thermal asymmetric interlaced PCR, and Touchdown PCR. In some embodiments, the polynucleotide amplification technique is LCR.

In some embodiments, the polynucleotide amplification technique comprises a mass spectroscpopy detection step following amplification. Such methods include but are not limited to those described in U.S. Pat. Nos. 7,108,974; 7,217,510; 7,226,739; 7,255,992; 7,312,036; 7,339,051; U.S. patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; 20080160512, 20080311558, 20090004643, 20090047665, 20090125245, 20090148829, 20090148836, 20090148837, 20090182511, WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; WO2007/100397; WO2007/118222, Ecker et al. (2005) "The Microbial Rosetta Stone Database: A compilation of global and emerging infectious microorganisms and bioterrorist threat agents" BMC Microbiology 5(1):19; Ecker et al. (2006) "The Ibis T5000 Universal Biosensor: An Automated Platform for Pathogen Identification and Strain Typing" JALA 6(11):341-351.; Ecker et al. (2006) "Identification of *Acinetobacter* species and genotyping of *Acinetobacter baumannii* by multilocus PCR and mass spectrometry" J Clin Microbiol. 44(8):2921-32.; Ecker et al. (2005) "Rapid identification and strain-typing of respiratory pathogens for epidemic surveillance" Proc Natl Acad Sci USA. 102(22):8012-7; Hannis et al. (2008) "High-resolution genotyping of *Campylobacter* species by use of PCR and high-throughput mass spectrometry" J Clin Microbiol. 46(4):1220-5; Blyn et al. (2008) "Rapid detection and molecular serotyping of adenovirus by use of PCR followed by electrospray ionization mass spectrometry" J Clin Microbiol. 46(2):644-51; Sampath et al. (2007) "Global surveillance of emerging Influenza virus genotypes by mass spectrometry" PLoS ONE 2(5):e489; Sampath et al. (2007) "Rapid identification of emerging infectious agents using PCR and electrospray ionization mass spectrometry" Ann N Y Acad Sci. 1102:109-20; Hall et al. (2005) "Base composition analysis of human mitochondrial DNA using electrospray ionization mass spectrometry: a novel tool for the identification and differentiation of humans" Anal Biochem. 344(1):53-69; Hofstadler et al. (2003) "A highly efficient and automated method of purifying and desalting PCR products for analysis by electrospray ionization mass spectrometry" Anal Biochem. 316:50-57; Hofstadler et al. (2006) "Selective ion filtering by digital thresholding: A method to unwind complex ESI-mass spectra and eliminate signals from low molecular weight chemical noise" Anal Chem. 78(2):372-378.; and Hofstadler et al. (2005) "TIGER: The Universal Biosensor" Int J Mass Spectrom. 242(1):23-41, each of which is herein incorporated by reference in its entirety.

Buffers or reaction mixtures that contain boric acid may further comprise any one or more additional reagents or components that find use in ampflication reactions. Examples, include, but are not limited to, single or double stranded template nucleic acid (RNA or DNA), primers, probes, labels, triphosphates, salts (e.g., KCl, Tris-HCl, $(NH_4)_2SO_4$), divalent cations ($Mg^{2+}$ and $Mn^{2+}$), control oligonucleotides, enzymes (e.g., polymerases, ligases, restriction enzymes, nucleases), solid supports (e.g., magnetic particles, beads, resins), and the like. In some embodiments, the present invention provides kits containing boric acid and one or more other amplification components in the appropriate packaging or containers. The boric acid may be provided alone (as a solid or dissolved in a liquid (e.g., water)), as part of a mixture with other salts and reagents, or in any desired form. Reagents may be provided in concentrated form (e.g., 5×, 10×, etc.) and are diluted prior to or during use.

BRIEF DESCRIPTION OF THE DRAWINGS

FIG. 1 shows mass spectronomy analysis of PCR products conducted in the presence or absence of boric acid.

DEFINITIONS

To facilitate an understanding of the present invention, a number of terms and phrases are defined below.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, etl al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the term "amplicon" refers to a nucleic acid generated using primer pairs. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the sequence of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers, the resultant amplicons having the primer sequences are used for subsequent analysis. In some embodiments, the amplicon further comprises a length that is compatible subsequent analysis (e.g., mass spectroscopy).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68: 90-99; the phosphodiester method of Brown et al. (1979) *Meth Enzymol.* 68: 109-151; the diethylphosphoramidite method of Beaucage et al. (1981) *Tetrahedron Lett.* 22: 1859-1862; the triester method of Matteucci et al. (1981) *J Am Chem Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein a "sample" refers to anything capable of being analyzed by the methods provided herein. In some embodiments, the sample comprises or is suspected to comprise one or more nucleic acids capable of analysis by the methods. In certain embodiments, for example, the samples comprise nucleic acids (e.g., DNA, RNA, cDNAs, etc.). Samples can include, for example, blood, semen, saliva, urine, feces, rectal swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

DETAILED DESCRIPTION OF THE INVENTION

The present invention addresses the problems associated with undesired polymerase based terminal transferase activity within a polynucleotide amplification setting (e.g., PCR; LCR). Indeed, experiments conducted during the course of developing embodiments for the present invention demonstrated that addition of boric acid to amplification reactions resulted in amplicons having reduced 3' non-template addition resulting from the polymerase dependent terminal transferase activity.

Accordingly, the present invention provides compositions (e.g., buffers, reactions mixtures, kits, systems) and methods for performing polynucleotide amplification (e.g., PCR) with boric acid or a boric acid equivalent as an additive so as to prevent 3' non-template nucleotide addition resulting from polymerase related terminal transferase activity.

The compositions and methods of the present invention are not limited to any particular source, type, and/or form of boric acid ($H_3BO_3$) (i.e., boracic acid, orthoboric acid, acidum boricum) or boric acid equivalents. In some embodiments, the boric acid and/or boric acid equivalent is provided in concentrated or diluted form, as a liquid or a solid (e.g., frozen solution, power). In some embodiments, the boric acid and/or boric acid equivalent is provided in a mixture of other salts or reagents.

The systems and methods of the present invention are not limited to particular amounts of boric acid or boric acid equivalents for use within polynucleotide amplification techniques (e.g., PCR) for inhibiting polymerase-related terminal transferase activity. In some embodiments, the amount of boric acid or boric acid equivalent used is sufficient to inhibit (e.g., diminish, reduce) polymerase related terminal transferase activity. In some embodiments, boric acid is provided dissolved in a primer dilution buffer (e.g., 50% primer dilution buffer) (e.g., 100 mM boric acid; 200 mM boric acid (see, e.g., Example I)).

The compositions and methods of the present invention provide a significant advantage to the field of polynucleotide amplification. For example, the use of boric acid within amplification reactions, such as PCR, to inhibit polymerase-based 3' non-template addition permits the use of a high concentration of magnesium salt as a PCR reagent. Use of boric acid within PCR to inhibit polymerase based 3' non-template addition reduces the heterogeneity of resulting PCR products (e.g., forward and reverse strands with only blunt ends) thereby reducing the complexity for product analysis techniques (e.g., high resolution mass spectrometry).

EXAMPLES

The invention now being generally described, will be more readily understood by reference to the following examples, which are included merely for purposes of illustration of certain aspects and embodiments of the present invention, and are not intended to limit the invention.

Example 1

PCR products with and without boric acid added to PCR components and reagents prior to thermal cycling steps were compared. Stock boric acid was dissolved in 50% primer dilution buffer and added to PCR reactions for a final concentration of 100 mM boric acid and 200 mM boric acid. FIG. 1 shows mass spectronomy analysis of PCR products conducted in the presence or absence of boric acid. As shown in FIG. 1, non-template addition on both the forward and reverse strands was identified in PCR products conducted in the absence of boric acid. As shown in FIG. 1, addition of boric acid resulted in PCR products with undetectable non-template addition on both the forward and reverse strands.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A kit comprising a PCR reaction solution, wherein said PCR reaction solution comprises boric acid, deoxynucleotide triphosphates, divalent cations, KCl and Tris-HCl or $(NH_4)_2SO_4$ and Tris-HCl, and a polymerase having terminal transferase activity.

2. The kit of claim 1, wherein said divalent cations are selected from group consisting of $Mg^{2+}$ and $Mn^{2+}$ divalent cations.

3. The kit of claim 1, wherein said polymerase having terminal transferase activity is Taq polymerase or a fragment thereof.

* * * * *